United States Patent [19]
Guildford et al.

[11] Patent Number: 4,736,057
[45] Date of Patent: Apr. 5, 1988

[54] CYCLOHEXANE DERIVATIVES

[75] Inventors: Allen J. Guildford, Sandbach; Ralph W. Turner, Cheadle, both of United Kingdom

[73] Assignee: Imperial Chemical Industries PLC, London, England

[21] Appl. No.: 670,017

[22] Filed: Nov. 9, 1984

[30] Foreign Application Priority Data

Nov. 11, 1983 [GB] United Kingdom ............... 8330099

[51] Int. Cl.$^4$ .............................................. C07C 69/76
[52] U.S. Cl. ...................................... 560/59; 560/102; 560/51; 560/56; 560/21; 560/45; 562/459; 562/469; 562/434; 562/450; 549/362; 549/434; 549/510
[58] Field of Search ................. 560/59, 102, 51, 56, 560/21, 45; 562/459, 469, 434, 400; 549/362, 434, 510; 514/532, 538, 568

[56] References Cited

U.S. PATENT DOCUMENTS 4,206,127 6/1980 Woessner .

FOREIGN PATENT DOCUMENTS 48572 3/1982 European Pat. Off. .
2004870 4/1979 United Kingdom .

*Primary Examiner*—Paul J. Killos
*Attorney, Agent, or Firm*—Cushman, Darby & Cushman

[57] ABSTRACT

This invention concerns novel (4-substituted-2-phenylcyclohexyl)alkenoic and alkanoic acid derivatives of the formula I wherein one of Ra and Rb is hydrogen, hydroxy, (1-6C)alkyl, (1-6C)alkoxy, (3-6C)alkenyloxy or phenyl(1-4C)alkoxy and the other of Ra and Rb is hydrogen, (1-6C)alkyl, (1-6C)alkoxy or (3-6C)alkenyloxy; or Ra and Rb together form a (2-4C)alkylenedioxy or oxo group; benzene ring X optionally bears a substituent selected from halogeno, (1-6C)alkyl, (1-6C)alkoxy, hydroxy, (2-6C)alkanoyloxy, (1-6C)alkanoylamino, trifluoromethyl and nitro; n is 3-5; Y is ethylene or vinylene; and in the cyclohexane ring, the substituents at positions 1 and 2 have cis- or trans-relative stereochemistry; and the pharmaceutically acceptable salts, (1-6C)alkyl esters and (1-6C)alkanesulphonamides thereof. The compounds of formula I possess valuable pharmacological properties of use in medicines. The invention also concerns processes for the manufacture of, and pharmaceutical compositions containing a novel compound of formula I.

10 Claims, No Drawings

CYCLOHEXANE DERIVATIVES

This invention relates to novel cyclohexane derivatives and, more particularly, to novel (4-substituted-2-phenylcyclohexyl)-alkenoic and -alkanoic acid derivatives which possess valuable pharmacological properties of use in medicine.

According to the invention there is provided an acid of the formula I set out hereinafter wherein one of Ra and Rb is hydrogen, hydroxy, (1-6C)alkyl, (1-6C)alkoxy, (3-6C) alkenyloxy or phenyl(1-4C)alkoxy and the other of Ra and Rb is hydrogen, (1-6C)alkyl, (1-6C)alkoxy or (3-6C)alkenyloxy; or Ra and Rb together form a (2-4C)alkylenedioxy or oxo group; benzene ring X optionally bears a substituent selected from halogeno, (1-6C)alkyl, (1-6C)alkoxy, hydroxy, (2-6C)alkanoyloxy, (1-6C)alkanoylamino, trifluoromethyl and nitro; n is 3-5; Y is ethylene or vinylene; and in the cyclohexane ring, the substituents at positions 1 and 2 have cis- or trans- relative stereochemistry; or a pharmaceutically acceptable salt, a (1-6C)alkyl ester or (1-6C)alkanesulphonamide of said acid.

In this specification the terms Ra, Rb et cetera are used to depict generic radicals and have no other meaning.

It will be appreciated that the compounds of formula I possess at least two asymmetric carbon atoms and may therefore exist in racemic and optically active forms. It is to be understood that the invention includes any racemic or optically active form of a compound of formula I which possesses the valuable pharmacological properties mentioned hereinafter, it being well known in the art how to prepare individual optically active forms (enantiomers), for example by synthesis from optically active starting materials, and how to determine the pharmacological properties using the standard tests mentioned below.

It will also be appreciated that when Y is vinylene the compounds of formula I may exist and be isolated in two geometric isomeric forms about the vinylene group (i.e. the so-called "E" and "Z" forms) or as a mixture of both forms. In general the processes of the invention for the production of the formula I compounds mentioned hereinafter produce mixtures of the geometric isomers in which the "Z" form predominates over the "E" form. However, it is to be understood that the invention includes compounds of formula I in either the "E" or the "Z" geometric form, or in mixtures thereof, which possess the valuable pharmacological properties mentioned hereinafter, it being well known in the art how to separate mixtures of geometric isomers, for example by chromatography.

A particular value for Ra or Rb when it is (1-6C)alkyl is, for example, methyl, ethyl, propyl or butyl.

A particular value for Ra or Rb when it is (1-6)alkoxy is, for example, methoxy, ethoxy, propoxy or butoxy and when it is (3-6C)alkenyloxy is, for example, allyloxy or 2-methylallyloxy.

A particular value for Ra or Rb when it is phenyl-(1-4C)alkoxy is, for example, benzyloxy, 1-phenylethoxy or 2-phenylethoxy.

A particular value for Ra and Rb when together they form a (2-4C)alkylenedioxy group is, for example, an ethylenedioxy or trimethylenedioxy group.

Particular values for optional substituents which may be present on benzene ring X are, for example:

for halogeno: fluoro, chloro or bromo;

for (1-6C)alkyl: methyl, ethyl, propyl, isopropyl, butyl, pentyl, or hexyl;

for (1-6C)alkoxy: methoxy, ethoxy, propoxy or butoxy;

for (2-6C)alkanoyloxy: acetoxy, propionyloxy or butyryloxy; and for (1-6C)alkanoylamino: formamido, acetamido or propionamido.

A preferred combination of n, and Y is, for example, when n is 3, and Y is cis-vinylene.

Particular pharmaceutically acceptable salts of acids of formula I are, for example, alkali metal and alkaline earth metal salts such as lithium, sodium potassium, magnesium and calcium salts, aluminium and ammonium salts, and salts with organic amines and quaternary bases forming physiologically acceptable cations such as salts with methylamine, dimethylamine, trimethylamine, ethylenediamine, piperidine, morpholine, pyrrolidine, piperazine, ethanolamine, triethanolamine, N-methylglucamine, tetramethylammonium hydroxide and benzyltrimethylammonium hydroxide.

Particular (1-6C)alkyl esters of acids of formula I are, for example, methyl, ethyl, propyl or butyl esters.

Particular (1-6C)alkanesulphonamides of acids of formula I are, for example, methanesulphonamides and ethanesulphonamides.

Typical compounds of the invention are described in the accompanying Examples. Of these a preferred compound is that described in Example 8.

The compounds of the invention may be manufactured by conventional procedures of organic chemistry well known in the art for the production of structurally analogous compounds. Such processes are provided as a further feature of the invention and are illustrated by the following preferred procedures in which Ra, Rb, benzene ring X, n, and Y have any of the aforesaid meanings:

(a) For a compound of formula I wherein Y is vinylene and Ra and Rb are other than an oxo group, reacting an aldehyde of the formula II wherein Rc and Rd have the same meanings as Ra and Rb apart from together as an oxo group, with a Wittig reagent of the formula:

$$Q_3P=CH.(CH_2)_n.CO_2^- M^+$$

wherein Q is (1-6C)alkyl or aryl (especially phenyl) and $M^+$ is a cation, for example, an alkali metal cation such as the lithium, sodium or potassium cation.

The process in general produces compounds of formula I in which the substituents adjacent to the double bond have predominantly cis-relative stereochemistry i.e. the "Z" isomer. However the compounds of formula I having trans-relative stereochemistry may also be obtained from the process by conventional separation of the mixture of cis- and trans- isomers first obtained.

The process is conveniently performed in a suitable solvent or diluent, for example an aromatic solvent such as benzene, toluene or chlorobenzene, an ether such as 1,2-dimethoxyethane, dibutyl ether or tretrahydrofuran, in dimethyl sulphoxide or tetramethylene sulphone, or in a mixture of one or more such solvents or diluents. The process is generally perfomed at a temperature in the range, for example, −80° C. to +40° C. but is conveniently performed at or near room temperature, that is in the range 15° to 35° C.

The proportion of the product of the process with trans-relative stereochemistry about the double bond may frequently be increased by choice of a suitable solvent, for example tetramethylene sulphone, and/or addition of an alkali halide, for example lithium bromide, to the reaction mixture.

(b) For a compound of formula I wherein one of Ra and Rb is (1-6C) alkoxy, (3-6C)alkenyloxy or phenyl(1-4C)alkoxy, reacting an alcohol of the formula III wherein Re has any of the meanings of Ra or Rb apart from hydroxy, with a compound of the formula Rf.Z wherein Rf is (1-6C)alkyl, (3-6C)alkenyl or phenyl(1-4C)alkyl and Z is a suitable leaving group, for example halogeno, alkanesuphonyloxy or arenesulphonyloxy, such as chloro, bromo, iodo, methanesulphonyloxy or p-toluenesulphonyloxy, in the presence of a suitable base.

A particular base which may be used is, for example of alkali metal hydride, (1-6C)alkyl lithium, alkali metal diisopropylamide or alkali metal t-butoxide, such as sodium hydride, methyl lithium, butyl lithium, lithium diisopropylamide or potassium t-butoxide.

The reaction is believed to involve intermediate formation of an alkali metal salt of the alcohol of formula III and this salt may conveniently be preformed by reaction with a stoichiometric amount of the base, prior to carrying out the reaction with the compound of formula Rf.Z. It will be understood that it is necessary to use at least two stoichiometric equivalents of the base unless the carboxylic acid group in the alcohol of formula III has first been protected as an ester group. It will further be understood that in such cases process (b) results in the production of an ester of the acid of formla I which may subsequently be hydrolysed, for example by reaction with aqueous alcoholic sodium or potassium hydroxide at a temperature in the range, for example, 10°-80° C., followed by acidification with a mineral acid to give the required acid of formula I.

Process (b) is preferably performed in a suitable solvent or diluent, for example as described for process (a) and at a temperature in the range, for example 10°-80° C. and conveniently at or near room temperature, that is in the range 15° to 35° C. (c) For a compound of formula I wherein one of Ra and Rb is hydroxy and the other is hydrogen, reducing a ketone of the formula IV or a salt, (1-6C)alkyl ester or (1-6C) alkanesulphonamide thereof.

The reduction may be carried out with any of a range of reducing agents well known in the art to be selective for oxo groups in the presence of other functional groups. Thus, for example, the reduction may be performed with an alkali metal borohydride or alkylborohydride, for example with lithium or sodium trisec-butylborohydride. In general a mixture of the epimeric hydroxy compounds of formula I wherein one of Ra and Rb is hydroxy and the other is hydrogen is produced, the proportion of one epimer to the other depending mainly on the reducing agent chosen. The individual epimers may be separated by known chromatographic procedures.

The reduction is normally performed in a suitable solvent, for example, ethanol, diethyl ether 1,2-dimethoxyethane or tetrahydrofuran and at a temperature in the range, for example, −80° C. to +30° C. (d) For a compound of formula I wherein Ra and Rb together form an oxo group, hydrolysing a ketal of the formula V or a (1-6C)alkyl ester or (1-6C)alkanesulphonamide thereof, wherein Rg and Rh are independently (1-6C)alkyl or together form (2-4C)alkylene.

The hydrolysis may be performed, for example in the presence of acid, for example an inorganic acid such as hydrochloric acid. A suitable solvent or diluent, for example, tetrahydrofuran, dioxan, acetone, methyl ethyl ketone, ethanol or 2-propanol may conveniently be used. The process is normally performed at a temperature in the range, for example 0° to 60° C.

(e) For a compound of formula I wherein Y is ethylene, a compound of formula I wherein Y is vinylene is hydrogenated in the presence of a suitable catalyst.

The process may be carried out in a suitable solvent or diluent, for example a (1-4C)alkanol such as ethanol or 2-propanol, optionally in the presence of water, and at a temperature in the range, for example, 15° to 35° C. using hydrogen at a pressure of, for example, 1 to 2 atmospheres.

A suitable catalyst is, for example, a noble metal catalyst such as palladium metal conveniently on an inert support such as carbon, barium sulphate or barium carbonate.

(f) For a compound of formula I wherein benzene ring X bears a hydroxy substituent, deprotecting a corresponding derivative of said compound wherein the hydroxy substituent is protected by a trimethylsilyl, (1-6C)alkyl (such as methyl or ethyl) or acyl (such as acetyl or benzoyl) protecting group.

The deprotection conditions required necessarily depend on the protecting groups concerned. Thus, for example, when it is methyl or ethyl (i.e. the starting material is the corresponding methoxy or ethoxy compound of formula I) the deprotection may be carried out, for example, by heating with sodium thiomethoxide in a suitable solvent (such as N,N-dimethylformamide) at an elevated temperature, for example 90°-160° C. Similarly, when the protecting group is acyl, it may be removed, for example by hydrolysis in the presence of a base (such as sodium or potassium hydroxide) in a suitable aqueous solvent [such as a (1-4C)alkanol or a glycol] at a temperature in the range, for example, 1 10°-60° C. Similarly, in the case of a trimethylsilyl protecting group, it may be removed for example, by reaction with aqueous tetrabutylammonium fluoride or sodium fluoride in conventional manner.

The necessary protected derivatives of the formula I compounds may be made by analogy with the other processes described herein.

The necessary starting materials for all the above processes may be obtained by conventional procedures well known in the art of organic chemistry. These procedures are illustrated in the accompanying reaction Schemes and Examples. In general a mixture of stereoisomers is produced in the reaction Schemes and it is necessary to separate out the individual stereoisomers using a conventional procedure such as chromatography at one or more stages in the Schemes.

The necessary Wittig reagents may be obtained by conventional procedures, for example by treating the corresponding phosphonium halides with a strong base such as sodium hydride, lithium diisopropylamide, potassium t-butoxide or butyllithium. They are generally formed in situ just prior to carrying out the condensation process (a).

When an ester or sulphonamide is required, the corresponding acid of formula I, conveniently as a reactive derivative thereof (such as its acid chloride, bromide, anhydride, mixed anhydride with formic acid or azide), is reacted with the appropriate (1-6C)alkanol or (1-6C)alkanesulphonamide (or with an alkali metal salt thereof).

Such a procedure may be carried out under conventional conditions, for example using an excess of the alkanol or sulphonamide and in a suitable solvent, for example tetrahydrofuran or 1,2-dimethoxyethane, and at a temperature in the range, for example, 10° to 100° C. When a compound of formula I is reacted in free acid form, a suitable dehydrating agent such as dicyclohexylcarbodiimide is normallly used to remove the water produced during the reaction. A suitable solvent or diluent which may then be used is, for example, tetrahydrofuran, pyridine, acetone, dichloromethane or 1,2-dimethoxyethane. When an alkali metal salt of the alkanol or sulphonamide is employed it is generally preferred to carry out the reaction in the presence of a polar solvent such as N,N-dimethylformamide or hexamethylphosphoramide. This procedure is particularly useful when a substituted sulphonamide is required. It is not normally necessary to provide external heating for those procedures in which a reactive derivative of an acid of formula I is employed.

When a salt of an acid of formula I is required, it is obtained by reaction with the appropriate base affording a physiologically acceptable cation, or by any other conventional procedure.

Further, when an optically active form of a compound of formula I is required, one of the aforesaid processes is carried out using an optically active starting material. Alternatively, a racemic form of an acid of formula I may be reacted with an optically active form of a suitable organic base, for example ephedrine, N,N,N-trimethyl (1-phenylethyl)ammonium hydroxide or 1-phenylethylamine, followed by conventional separation of the diastereoisomeric mixture of salts thus obtained, for example by fractional crystallisation from a suitable solvent, for example a (1-4C)alkanol, whereafter the optically active form of said acid of formula I may be liberated by treatment with acid using a conventional procedure for example using an aqueous mineral acid such as dilute hydrochloric acid.

When an optically active form of an ester or amide of an acid of formula I is required, it may be obtained using the aforementioned esterification or amidification procedures starting from the appropriate optically active form of said acid.

Many of the intermediates defined herein are novel and are provided as further separate features of the invention.

As stated above, the acids of the invention possess valuable pharmacological properties of use in medicine. In particular the acids of formula I antagonise to varying degrees the actions of thromboxane $A_2$ (referred to below as "$TXA_2$") for example certain of its actions on blood platelets, the vasculature and/or the lung.

It is known that $TXA_2$ is a potent aggregator of blood platelets and a powerful vasoconstrictor. $TxA_2$ is also a potent constrictor of bronchial and tracheal smooth muscle. $TXA_2$ may therefore be involved in a wide variety of disease conditions, for example ischaemic heart disease such as myocardial infarction and angina, cerebro-vascular disease such as transient cerebral ischaemia, migraine and stroke, peripheral vascular disease such as atherosclerosis, arteriosclerosis, microangiopathy, hypertension and blood clotting defects due to lipid imbalance, and pulmonary disease such as pulmonary embolism, bronchial asthma, bronchitis, pneumonia, dyspnoea and emphysema. Accordingly, compounds which antagonise the actions of $TXA_2$ may be expected to have therapeutic value in the prevention or treatment of any one or more of the above mentioned diseases or any other disease conditions in which it is desirable to antagonise the actions of $TXA_2$.

The $TXA_2$ antagonism may be demonstrated in one or other of the following standard tests:

(a) The rabbit aortal strip model devised by Piper and Vane (*Nature.* 1070. 223, 29-35) using as agonist the $TXA_2$ mimetic agent known as U46619 (R. L. Jones et alia in "Chemistry, Biochemistry and Pharmacological Activity of Prostanoids", eds. S. M. Roberts and F. Scheinman, at p.211, Pergamon Press, 1979);

(b) a blood platelet aggregation test based on that described by Born *Nature,* 1962, 194, 927-929) and involving mesuring the inhibition by a test compound of aggregation of citrated, platelet rich human plasma induced by a sub-maximal concentration (in the range 25-100 $\mu$/ml.) of arachidonic acid; and (c) a bronchoconstriction test involving measuring the inhibition by a test compound of the bronchoconstriction induced in the Konzett-Rossler guinea-pig model (as modified by Collier and James, *Brit. J. Pharmacol.,* 1967, 30, 283-307) by intravenous administration of the $TXA_2$ mimetic agent, U46619 at 1-1.5 $\mu$g/kg.

Similarly, the antagonism of the effects of $TXA_2$ on the vasculature may be demonstrated in the following manner:

(d) Male rats (Alderley Park strain) are anaesthetised with sodium pentobarbital and blood pressure is monitored at the carotid artery. The $TXA_2$ mimetic agent known as U46619 is administered intravenously via the jugular vein and an $ED_{50}$ (dose necessary to produce 50% of the maximum hypertensive effect) is established (n=3). The $ED_{50}$ for U46619 is approximately 5 $\mu$g/kg. A test compound is then administered either intravenously via the jugular vein or orally via a cannula directly into the stomach and the animal challenged with an $ED_{50}$ dose of U46619, five minutes after dosing with test compound and then successively every ten minutes until the hypertensive effect of U46619 is no longer blocked.

In general, acids of formula I (and salts, esters and amides thereof) show significant activity in one or more of the above tests without any sign of overt toxicity at the active dose in tests (c) or (d).

By way of example the compound of formula I described in Example 16 hereafter gives a $pA_2$ of 5.9 in test (a).

As stated previously, the acids of formula I may be used in the therapy or prevention of diseases or adverse conditions in warm-blooded animals in which it is desirable to antagonise one or more of the actions of $TXA_2$. In general, an acid of formula I will be administered for this purpose by an oral, rectal, intravenous, subcutaneous, intramuscular or inhalation route, so that a dose in the range, for example 0.5-30 mg./kg. body weight, will be given up to four times per day, varying with the route of administration, the severity of the condition and the size and age of the patient under treatment.

The acids of formula I will generally be used in the form of a pharmaceutical composition comprising an acid of formula I or, where appropriate a salt, ester or sulphonamide thereof as defined hereinbefore, together with a pharmaceutically acceptable diluent or carrier. Such compositions are provided as a further feature of the invention and may be in a variety of dosage forms. For example, they may be in the form of tablets, capsules, solutions or suspensions for oral administration; in the form of suppositories for rectal administration; in the form of sterile solutions or suspensions for administration by intravenous or intramuscular injection; in the form of aerosols or nebuliser solutions or suspensions for administration by inhalation; and in the form of powders together with pharmaceutically acceptable inert solid diluents such as lactose for administration by insufflation.

The pharmaceutical compositions may be obtained by conventional procedures using pharmaceutically acceptable diluents and carriers well known in the art. Tablets and capsules for oral administration may conveniently be formed with an enteric coating, for example comprising cellulose acetate phthalate, to minimise contact of the active ingredient of formula I with stomach acids.

The pharmaceutical compositions of the invention may also contain one or more agents known to be of value in diseases or conditions intended to be treated; for example, a known platelet aggregation inhibitor, hypolipidaemic agent, anti-hypertensive agent, betaadrenergic blocker or a vasodilator may usefully also be present in a pharmaceutical composition of the invention for use in treating a heart or vascular disease or condition. Similarly, by way of example, an antihistamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

In addition to their use in therapeutic medicine the acids of formula I are also useful as pharmacological tools in the development and standardisation of test systems for the evaluation of the effects of $TXA_2$ in laboratory animals such as cats, dogs, rabbits, monkeys, rats and mice, as part of the search for new therapeutic agents. The acids of formula I may also be used because of their $TXA_2$ antagonist properties in helping to maintain the viability of blood and blood vessels in warm-blooded animals (or parts thereof) under-going artificial extracorporeal circulation, for example during limb or organ transplants. When used for this purpose an acid of formula I, or a physiologically acceptable salt thereof, will generally be administered so that a steady state concentration in the range, for example, 0.5 to 50 mg. per liter is achieved in the blood.

The invention will now be illustrated in the following non-limiting Examples in which, unless otherwise stated:

(i) evaporations were carried out by rotary evaporation in vacuo;

(ii) operations were carried out at ambient temperature, that is in the range 18°–26° C.;

(iii) column chromatography was performed on Merck Kieselgel 60 (Art, 7734) using approximately 50–70 g. of $SiO_2$ per g. of sample, and monitoring the process by thin layer chromatography on Merck 0.25 mm. Kieselgel 60F 254 plates (Art. 5715), flash chromatography was performed on Merck Kieselgel (Art 9385); these materials were obtained from E. Merck, Darmstadt, W. Germany;

(iv) yields are given for illustration only and are not necessarily the maximum attainable;

(v) NMR spectra were normally determined at 400 MHz in $CDCl_3$ using tetramethylsilane (TMS) as an internal standard, and expressed as chemical shifts (delta values) in parts per million relative to TMS using the following abbreviations for designation of major peaks: s, singlet; m, multiplet; t, triplet; br, broad; d,doublet; when a single chemical shift value is given for a multiplet (m) this corresponds to the centre point of the signals making up the multiplet; and (vi) end products were isolated as racemates.

EXAMPLE 1

(Cis-2-phenylcyclohexyl)acetaldehyde (1.42 g.) in dry dimethylsulphoxide (7 ml.) was added under argon with stirring to a solution of the ylid prepared from (4-carboxybutyl)triphenylphosphonium bromide (9.31 g.) and dimsyl sodium solution [generated from a 50% w/w sodium hydride and mineral oil dispersion (2.0 g.) and dry dimethylsulphoxide (50 ml.)] and the mixture was stirred overnight. Cautious addition of water (500 ml.) followed by extraction with ether removed the bulk of the neutral material. The aqueous layer was acidified to pH2 with 2M-hydrochloric acid and extracted with ether (3×150 ml.). The combined extracts were washed with water, dried ($MgSO_4$) and evaporated to give a yellow oil, which was purified by flash column chromatography on silica, eluting with ether/hexane (1:1 v/v) to give a colourless oil which was crystallised from pentane. There was thus obtained 5(Z)-7-(cis-2-phenylcyclohexyl)heptenoic acid (1.25 g.), m.p. 45°–48° C.; NMR ($CDCl_3$) : 1.33–2.11 (15H,m), 2.24 (2H,t), 2.89 (1H, d of t, Jaa=11Hz, Jae=4 Hz, Jae=4 Hz) 5.22 (2H,m), 7.18 (3H,m) and 7.28 (2H,m).

The starting material was obtained as follows:

A stirred suspension of (cis-2-phenylcyclohexyl)acetic acid (15 g.) in dry toluene (100 ml.),cooled at −10° C. under argon, was treated with a 3.46 M solution of sodium bis(2-methoxyethoxy)aluminium hydride in toluene (25 ml.). The mixture was stirred overnight, diluted with ice/water (50 ml.), acidified with concentrated hydrochloric acid to pH 2. and extracted with ethyl acetate (3×150 ml.). The extracts were combined, washed with water (3×100 ml.), dried ($MgSO_4$) and the solvent removed by evaporation to give 2-(cis-2-phenylcyclohexyl)ethanol (10.3 g.), which solidified on standing to give material of m.p. 48°–50° C.; NMR ($CDCl_3$): 1.08–2.0 (12H,m), 2.81 (1H, d of t, Jaa=11 Hz, Jae=4 Hz, Jae=4 Hz, indicating cis-relative stereochemistry about the cyclohexane ring), 3.21 (1H,m), 3.37 (1H, m), 7.09 (3H,m), and 7.22 (2H,m).

A solution of 2-(cis-2-phenylcyclohexyl)ethanol (3 g.) in methylene chloride (6 ml.) was added rapidly to a stirred suspension of pyridinium chlorochromate (4.8 g.) in methylene chloride (6 ml.). The mixture was stirred for 2 hours and diluted with ether (75 ml.). The supernatant solution was decanted from the black tar and filtered through diatomaceous earth. The residual tar was washed thoroughly with ether. The combined ethereal filtrate and washings were evaporated. The pale yellow oil obtained, was purified by flash chromatography on silica eluting with hexane/ether (2:1 v/v) to give (cis-2-phenylcyclohexyl)acetaldehyde (1.5 g.) as a semi-solid; NMR ($CDCl_3$): 1.1–2.35 (10H, m), 2.4–2.7 (1H,m), 2.75–3.0 (1H,m), 7.0–7.4 (5H,m) and 9.3 (1H, br s).

EXAMPLE 2

Using a similar procedure to that described in Example 1, but using (4-carboxypentyl)triphenylphosphonium bromide in place of (4-carboxybutyl)triphenylphosphonium bromide, there was obtained 6(Z)-8-(cis-2-phenylcyclohexyl)oct-6-enoic acid as an oil in 36% yield; NMR (CDCl$_3$): 1.06–2.14 (17H,m), 2.16–2.40 (2H,t), 2.72–3.00 (1H,m), 5.00–5.44 (2H,m) and 7.0–7.4 (5H, br s); mass spectrum, m/e 300.2088, theory: 300.2089.

EXAMPLE 3

A stirred solution of 5(Z)-7-(cis-2-phenylcyclohexyl)-heptenoic acid (200 mg.) in absolute ethanol (2 ml.) was hydrogenated at atmospheric pressure over a 5% w/w palladium-on-charcoal catalyst (20 mg.) until no more hydrogen was absorbed. The mixture was filtered through diatomaceous earth and the filtrate was evaporated to give 7-(cis-2-phenylcyclohexyl)heptanoic acid as a colourless oil (200 mg.); NMR (CDCl$_3$): 0.82–1.88 (19H,m), 2.22–2.30 (2H,t), 2.75–2.88 (1H, d of t, Jaa=11 Hz Jae=4 Hz Jae=4 Hz), 7.15–7.25 (3H, br s) and 7.3–7.4 (2H, br s).

EXAMPLE 4

Using a similar method to that described in Example 1, but starting from (trans-2-phenyl-4,4-dimethylcyclohexyl)acetaldehyde in place of (cis-2-phenylcyclohexyl)acetaldehyde, there was obtained, 5(Z)-7-(trans-2-phenyl-4,4-dimethylcyclohexyl)heptenoic acid as an oil, containing ca 10% of 5(Z)-7-(cis-2-phenyl 4,4-dimethylcyclohexyl)heptenoic acid (yield 32%); NMR (CDCl$_3$): 2.45 (1H, t of d, Jaa=11Hz, Jaa=11Hz, Jae=4 Hz, trans Ph-CH), 3.1 (1H, d of t, cis Ph-CH).

The aldehyde starting material was obtained as follows:

A stirred solution of 4,4-dimethylcyclohexanone (1 g.), p-toluene sulphonic acid monohydrate (23 mg.) and thiophenol (0.81 ml.) in toluene (24 ml.) was heated at reflux for 9 hours with azeotropic removal of water using a Dean and Stark apparatus. The mixture was cooled, diluted with toluene (25 ml.) and extracted with saturated sodium bicarbonate solution (2×10 ml.), washed with water (3×10 ml.) and dried (MgSO$_4$). Evaporation of the solvent gave (4,4-dimethylcyclohex-1-enyl)phenylsulphide as an oil (1.66 g.); NMR (CDCl$_3$,90 MHz): 0.94 (6H,s), 1.45 (2H,t), 1.98 (2H,m), 2.18 (2H,m), 6.02 (1H,m) and 7.3 (5H,m).

A stirred solution of (4,4-dimethylcyclohex-1enyl)-phenyl sulphide (1.66 g.) in methanol (30.5 ml.) cooled at 0° C., was treated dropwise with a solution of potassium hydrogen persulphate ("Oxone" brand, containing 2KHSO$_5$. KHSO$_4$.K$_2$SO$_4$; "Oxone" is a registered trademark) (9.0 g.) in distilled water (30.5 ml.) at such a rate as to maintain the reaction temperature below 5° C. After the addition was complete, the reaction was stirred for 64 hours. The methanol was then evaporated and the residue was diluted with water (50 ml.) before extraction with ether (3×100 ml.). The combined extracts were washed successively with saturated sodium bicarbonate solution (3×50 ml.) and water (3×50 ml.), dried (MgSO$_4$) and evaporated. The residue obtained was purified by flash chromatography on silica, eluting with ether hexane (40:60 v/v), to give (4,4-dimethyl-cyclohex-1-enyl)phenyl sulphone (1.52 g.), m.p. 51°–53° C.; NMR (CDCl$_3$): 0.9 (6H,s), 1.45 (2H,t), 2.0–2.3 (4H,m), 7.0 (1H,br s), 7.4–7.7 (3H,m) and 7.8–8.0 (2H,m).

A solution of (4,4-dimethyl-cyclohex-1-enyl)phenyl sulphone (11.2 g.) in sodium dried ether (56 ml.) was added dropwise over 10 minutes to an ice cooled, stirred 0.603 M ethereal solution (78 ml.) of phenyl lithium. The mixture was then stirred at ambient temperature for one hour before dropwise addition of allyl bromide (7.71 ml.) during 5 minutes, with cold water bath cooling. The reaction mixture was stirred for 30 minutes before cautious addition of ice/water (100 ml.) and extraction with ether (3×100 ml.). The combined extracts were washed with water (3×75 ml.) dried (MgSO$_4$) and evaporated to give an oil which was purified by flash chromatography on silica, eluting with toluene. There was thus obtained 3-(1-phenylsulphonyl-2-phenyl-4,4-dimethylcyclohexyl)-1-propene as a solid mixture (9:1) of stereoisomers after recrystallisation from ethanol (6.9 g.);m.p. 152°–160° C.; partial NMR (Ph.CH signals): 3.82 (1H, d of d,Jaa=13 Hz; major isomer) 3.25 (1H, d of d, Jaa=13 Hz; minor isomer).

To a stirred solution of 3-(1-phenylsulphonyl-2-phenyl-4,4-dimethylcyclohexyl)-1-propene (6.5 g.) in dry tetrahydrofuran (88 ml.) in an atmosphere of argon were added consecutively, anhydrous disodium hydrogen phosphate (10.06 g.), 5% w/w sodium amalgam (31.85 g.) and dry methanol (176 ml.). The mixture was stirred for 3 hours when further additions of disodium hydrogen phosphate (10.06 g.) and 5% w/w sodium amalgam (31.85 g.) were made and stirring was continued for 1 hour. The supernatant reaction mixture was then decanted from unreacted sodium amalgam and solvents removed by evaporation. The residue was diluted with water (200 ml.) and extracted with ether (3×100 ml.). The combined extracts were washed with water (2×50 ml.), dried (MgSO$_4$) and evaporated. The residue obtained was purified by flash chromatography on silica, eluting with hexane, to give a mixture containing >85% [as estimated by gas chromatography (GC) of the required 3-(trans-2-phenyl-4,4-dimethylcyclohexyl)-1-propene(2.81 g.); partial NMR (CDCl$_3$): 2.45 (1H, t of d, Jaa=12 Hz, Jaa=12 Hz , Jae=4 Hz, trans-Ph.CH); mass spectrum, m/e: 228.1861; theory (C$_{17}$H$_{24}$): 228.1878.

Ozone was passed through a stirred solution of 3-(trans-2-phenyl-4,4-dimethylcyclohexyl)-1-propene (1.4 g.) in dichloromethane (35 ml.) at −78° C. until a permanent blue colour developed. The solution was then flushed with argon until colourless. A solution of triphenylphosphine (2.01 g.) in dichloromethane (10 ml.) was then added and the mixture left at 0°–5° C. overnight. The mixture was then purified by flash chromatography on silica, eluting with ether/hexane (5:95 v/v) to give a mixture containing 95% (estimated by GC) of the required (trans-2-phenyl-4,4-dimethylcyclohexyl)acetaldehyde (0.963 g.); partial NMR (CDCl$_3$): 2.5 (1H, t of d, Jaa=11 Hz, Jaa=11 Hz, Jae=4 Hz, trans-Ph.CH).

EXAMPLE 5

Using a similar method to that described in Example 1, but starting from (trans-2-phenylcyclohexyl)acetaldehyde (contaminated with <10% cis-isomer) in place of (cis-2-phenylcyclohexyl)acetaldehyde, there was obtained 5(Z)-7-(trans-2-phenylcyclohexyl)heptenoic acid containing <10% of 5(Z)-7-(cis-2-phenylcyclohexyl)-hept-5-enoic acid, as a colourless oil in 38% yield; partial NMR (CDCl$_3$): 2.21 (1H, t of d, Jaa=12 Hz, Jaa=12 Hz, Jae=4 Hz, trans-Ph.CH), 2.88 (1H, d of t, Jaa=12 Hz, Jae=4 Hz, Jae=4 Hz, cis-Ph.CH); mass spectrum, m/e 286.1949, theory: 286. 1932.

The starting material was obtained using an analogous procedure to that described in Example 4, but starting from 1-phenylsulphonyl-cyclohexene. The following intermediates analogous to those described in Example 4 were isolated:

(a) 3-(1-phenylsulphonyl-2-phenylcyclohexyl)-1-propene, as a mixture of stereoisomers, m.p. 149°-153° C.;

(b) 3-(trans-2-phenylcyclohexyl)-1-propene contaminated with <10% of 3-(cis-2-phenylcyclohexyl)-1-propene.

(c) (trans-2-phenylcyclohexyl)acetaldehyde contaminated with 10% (cis-2-phenylcyclohexyl)acetaldehyde (as indicated by GC); partial NMR (CDCl$_3$): 9.45 (1H, br s, trans CHO; 9.35 (1H, br s, cis-CHO).

EXAMPLE 6

A suspension of (4- carboxybutyl)triphenylphosphonium bromide (19.95 g.) and potassium t-butoxide (10.1 g.) in dry tetrahydrofuran (445 ml.) was stirred under argon for 30 minutes. The resultant orange coloured ylid suspension was cooled to 10° C. and a solution of the ethylene ketal of (4-keto-2-phenyl-cis-cyclohexyl)acetaldehyde (3.9 g.) in dry tetrahydrofuran (180 ml.) was added dropwise, at such a rate as to maintain the reaction temperature at 10° C. After stirring at 10° C. for 1 hour, water (150 ml.) was added and the solvent was evaporated. The residue was diluted with water (150 ml.) and then extracted with ether to remove most of the neutral material. The aqueous layer was separated, acidified with acetic acid and extracted with ether ( 3×150 ml.). The combined extracts were washed successively with water ( 2×75 ml.) and brine (1×75 ml.), dried (MgSO$_4$) and evaporated under reduced pressure. The residue was purified by flash chromatography on silica, eluting with ether/hexane/acetic acid (50:50:0.5) to give the ethylene ketal of 5-(Z)-7-(4-keto-2-phenyl-cis-cyclohexyl)heptenoic acid (2.96 g.), after recrystallisation from hexane, m.p. 62°-64° C.; NMR: (CDCl$_3$): 1.42-2.38 (15H,m), 3.1-3.4 (1H,d of t), 3.94 (4H,s), 4.95-5.45 (2H,m), 7.0-7.4 (5H,m) and 9.15 (1H,br s).

The starting aldehyde was obtained as follows:

(i) A stirred solution of ethyl (4-keto-2-phenyl cyclohex-2-enyl)acetate (12.91 g.), p-toluene sulphonic acid monohydrate (0.95 g.) and ethylene glycol (2.93 ml.) in benzene (258 ml.) was heated under reflux using a Dean and Stark water separator for 2.5 hours. A further aliquot of ethylene glycol (0.7 ml.) was then added and the mixture heated under reflux for a further 3 hours. The reaction mixture was then cooled and the benzene evaporated. The residual mixture was dissolved in ether (500 ml.). The solution was extracted with saturated sodium bicarbonate solution (2×100 ml.). The combined extracts were washed with water (2×100 ml.), dried (MgSO$_4$) and evaporated under reduced pressure. The crude product was purified by flash chromatography on silica, eluting with ether/hexane (3:1 v/v), to give the ethylene ketal of ethyl (4-keto-2-phenylcyclohex-1-enyl)acetate (9.35 g.) NMR (90 MHz): 1.20 (3H,t), 1.88 (2H,t). 2.38 (2H,t), 2.9 (2H,s), 4.0 (4H,s), 4.1 (2H,q) and 7.1-7.4 (5H,)ppm.

(ii) A stirred solution of the ethylene ketal of ethyl (4-keto-2-phenylcyclohex-1-enyl)-acetate (7.0 g.) in ethyl acetate (70 ml.) was hydrogenated at atmospheric pressure over a 5% w/w palladium-on-charcoal catalyst (0.7 g.) for 16 hours. The mixture was filtered through diatomaceous earth and the filtrate was evaporated. The residue was purified by flash chromatography on silica, eluting with ether/hexane (4:6 v/v), to give the ethylene ketal of ethyl (4-keto-2-phenyl-cis-cyclohexyl)acetate (6.2 g.), as a colourless solid, m.p. 83°-86° C.; NMR (CDCl$_3$): 3.29 (1H, d of t, Jaa=13 Hz, Jae=3 Hz, Jae=3 Hz, cis-Ph.CH); mass spectrum: m/e 304.

(iii) A stirred solution of the ethylene ketal of ethyl (4-keto-2-phenyl-cis-cyclohexyl)acetate (5.0 g.) in dry toluene (100 ml.), cooled at −70° C. under argon, was treated dropwise with a 1M solution of diisobutylaluminium hydride in toluene (18 ml.). The mixture was stirred at −70° C. for 35 minutes, quenched by addition of ethanol (5 ml.) and allowed to warm up to ambient temperature. Water (100 ml.) was then added and the subsequent mixture was extracted with ether (4×100 ml.). The combined extracts were washed successively with water (2×100 ml.) and brine (1×100 ml.), dried (MgSO$_4$) and evaporated. The residue obtained was purified by flash chromatography on silica, eluting with ether/hexane (3:7 v/v), to give the ethylene ketal of (4-keto-2-phenyl-cis-cyclohexyl)acetaldehyde (3.92 g.) which was used immediately in the Wittig reaction.

EXAMPLE 7

A solution of the ethylene ketal of 5(Z)-7-(4-keto-2-phenyl-cis-cyclohexyl)hept-5-enoic acid (2.5 g.) in 2M aqueous hydrochloric acid (200 ml.) and dioxan (200 ml.) was stirred for one hour. The mixture was then diluted with water (500 ml.) and extracted with ether (3×250 ml.). The combined extracts were washed successively with water (2×100 ml.), brine (1×100 ml.), dried (MgSO$_4$) and evaporated. The residue obtained was purified by flash chromatography on silica, eluting with ether/hexane/acetic acid (50:50:0.5 v/v ). Any residual acetic acid after evaporation of the eluate fractions was removed by azeotropic distillation with toluene. There was thus obtained 5(Z)-7-(4-keto-2-phenyl-cis-cylohexyl)heptenoic acid as a colourless solid (1.99 g. after washing with hexane), m.p. 84°-86° C.; NMR (CDCl$_3$): 1.62 (2H,m), 1.9 (6H,m), 2.1 (1H,m), 2.27 (2H,t), 2.37(1H,m), 2.48 (1H,m), 2.60 (1H,m), 2.75 (1H,m), 3.4 (1H,m), 5.33 (2H,m), 7.08 (2H,d) and 7.18-7.33 (3H,m).

EXAMPLE 8

A solution of sodium borohydride (13 mg.) in absolute ethanol (0.5 ml.) was added to a stirred solution of 5(Z)-7-(4-keto-2-phenyl-cis-cyclohexyl)heptenoic acid (100 mg.) in absolute ethanol (2 ml.), cooled at 0° C. After stirring at 0° C. for one hour, a further aliquot of sodium borohydride (2.6 mg.) in absolute ethanol (0.1 ml.) was added and stirring continued at 0° C. for a further 30 minutes. The reaction mixture was then added to water (20 ml.). The aqueous mixture was adjusted to pH 2 with concentrated hydrochloric acid and extracted with ether (3×20 ml.). The combined extracts were washed with water (2×15 ml.), dried (MgSO$_4$) and evaporated. The residual oil was purified by preparative thin layer chromatography on two 20 cm×20 cm×0.25 mm silica plates, Merck Art No. 5715), developing with ether/hexane (4:1 v/v ), to give 5(Z)-7-([1,2,4-cis]-4-hydroxy-2-phenylcyclohexyl)heptenoic acid as an oil (55 mg.): NMR (CDCl$_3$) 1.38-2.27 (15H,m), 2.93 (1H, d of t, Jaa=13 Hz, Jae=3 Hz, Jae=3 Hz) , 3.75 (1H, t of t, Jaa=11Hz, Jaa=11Hz, Jae=4 Hz, Jae=4 Hz), 3.85-4.53 (br s), 5.1 (1H,m), 5.27 (1H,m) and 7.13-7.33 (5H,m).

EXAMPLE 9

A stirred solution of 5(Z)-7-(4-keto-2-phenyl cis-cyclohexyl)heptenoic acid (200 mg.) in dry tetrahydrofuran (20 ml.), cooled to −78° C. under argon, was treated dropwise with a 1M solution (1.34 ml.) of lithium tri-sec-butylborohydride and stirred at −78° C. for 3 hours before addition of absolute ethanol (2 ml.). The reaction mixture was allowed to warm up to ambient temperature, and was then acidified with 10% v/v aqueous hydrochloric acid. The mixture was shaken vigorously for 5 minutes, diluted with water (50 ml.) and extracted with ether (3×50 ml.). The combined extracts were washed successively with water (2×50 ml.) and brine (50 ml.), dried (MgSO₄) and evaporated. The residue was purified by flash chromatography on silica, eluting with ether/hexane/acetic acid (50:50:0.5 v/v), to give 5(Z)-7-(cis-2-phenyl-trans-4-hydroxycyclohexyl)heptenoic acid (110 mg. after recrystallisation from ether/hexane), m.p. 91°–93° C.; NMR (CDCl₃): 1.5–2.1 (14H,m), 2.2 (2H,t), 3.35 (1H, d of t Jaa=12 Hz, Jae=4 Hz, Jae=4 Hz), 4.25 (1H,m), 5.25 (2H,m) and 7.13–7.32 (5H,m).

EXAMPLE 10

Using a similar procedure to that described in Example 6, but starting from the ethylene ketal of (4-keto-2-phenyl-trans-cyclohexyl)acetaldehyde, there was obtained the ethylene ketal of 5(Z)-7-(4-keto-2-phenyl-trans-cyclohexyl)heptenoic acid, in 86% yield; NMR (CDCl₃): 1.28–1.93 (15H,m), 2.23 (2H, t), 2.55 (1H,t of d, Jaa=11 Hz, Jaa=11 Hz, Jae=3 Hz), 3.95 (4H, br s), 5.3 (2H, br s) and 7.13–7.3 (5H,m).

The starting material was obtained as follows:

(i) A solution of phenyl magnesium bromide was prepared in the usual way from bromobenzene (1.24 ml.), magnesium (0.564 g.) and dry tetrahydrofuran (22 ml.) under argon. The stirred solution was cooled to −20° C. Dry cuprous iodide (0.113 g.) was added and the mixture was stirred at −20° C. for 5 minutes before dropwise addition of a solution (A) of methyl (4-ketocyclohex-2-enyl)acetate (1.98 g.) in dry tetrahydrofuran (2 ml.) at such a rate as to maintain the reaction temperature at −18° to −20° C. Two additional portions of dry cuprous iodide (0.113 g.) were added following addition of ⅓ and ⅔ of the solution A. The mixture was stirred at −20° C. for 5 minutes and then added to ice cold saturated ammonium chloride solution (63 ml.). The mixture obtained was extracted with ether (3×100 ml.). The combined extracts were washed successively with saturated ammonium chloride solution (2×50 ml.) and brine (50 ml.), dried (MgSO₄) and evaporated. The residual oil was purified by flash chromatography on silica, eluting with ethyl acetate/toluene (15:85 v/v), to give methyl (4-keto-2-phenyl-trans-cyclohexyl) acetate as a colourless oil which solidified on trituration with hexane/ether to give a solid (1.19 g.), m.p. 45°–47° C.; NMR (CDCl₃, 90 MHz): 1.9–2.8 (10H,m), 3.55 (3H,s), 7.0–7.4 (5H,m).

(ii) A stirred solution of methyl (4-keto-2-phenyl-trans-cyclohexyl)acetate (1.0 g.), p-toluene sulphonic acid monohydrate (77 mg.) and ethylene glycol (0.238 ml.) in benzene (40 ml.) was heated for 1 hour under reflux in argon, using a Dean and Stark water separator. The mixture was then cooled, benzene removed by evaporation and the residual material diluted with ether (200 ml.). The solution obtained was washed with saturated sodium bicarbonate solution (50 ml.), brine (50 ml.) and then dried (MgSO₄) and evaporated under reduced pressure. The crude product was purified by flash chromatography on silica, eluting with ether/hexane (1:1 v/v) to give, after trituration with hexane at −70° C., the ethylene ketal of methyl (4-keto-2-phenyl-trans-cyclohexyl) acetate (1.02 g.), m.p. 53°–55° C.; NMR (CDCl₃):1.2–2.3 (9H,m), 2.35–2.8 (1H,m), 3.5 (3H,s) 3.9 (4H,s) and 7.0–7.4 (5H,m).

(iii) Using a similar procedure to that described for the analogous starting material in part (iii) in Example 6, but using the ethylene ketal of methyl (4-keto-2-phenyl-trans-cyclohexyl)acetate there was obtained the ethylene ketal of (4-keto-2-phenyl-trans-cyclohexyl)acetaldehyde, as a colourless oil in 81% yield; NMR (CDCl₃): 1.3–2.1 (7H,m), 2.18 (2H,br s), 2.4–2.8 (1H,m), 3.95 (4H,s), 7.06–7.44 (5H,m) and 9.48 (1H,br s).

EXAMPLE 11

Using a similar procedure to that described in Example 7, but starting from the ethylene ketal of 5(Z)-7-(4-keto-2-phenyl-trans-cyclohexyl)heptenoic acid there was obtained 5(Z)-7-(4-keto-2-phenyl-trans-cyclohexyl)heptenoic acid, as a colourless oil in 86% yield; NMR (CDCl₃): 1.4–2.58 (15H,m), 2.68 (1H,t of d, Jaa=11 Hz, Jaa=11 Hz, Jae=5 Hz,), 5.32 (2H,m) and 7.12–7.35 (5H,m).

EXAMPLE 12

Using a similar procedure to that described in Example 8, but starting from 5(Z)-7-(4-keto-2-phenyl-trans-cyclohexyl)heptenoic acid, there was obtained, 5(Z)-7-(cis-4-hydroxy-trans-2-phenylcyclohexyl)heptenoic acid, as a colourless oil in 64% yield; NMR (CDCl₃): 1.05–2.35 (16H,m), 3.68 (1H,t of t, Jaa=11 Hz, Jaa=11 Hz, Jae-4 Hz, Jae=4 Hz), 5.27 (2H,m) and 7.12–7.32 (5H,m).

EXAMPLE 13

A stirred solution of 5(Z)-7-([1,2,4-cis]-4-hydroxy-2-phenylcyclohexyl)heptenoic acid (96 mg.) in dry tetrahydrofuran (4 ml.) under argon was treated portionwise with 50% w/w sodium hydride in mineral oil dispersion (32.4 mg.). After 2 hours methyl iodide (21 microliters.) was added and the mixture stirred for 16 hours. A further portion of methyl iodide (15 microliters) was then added and stirring continued for 24 hours. The reaction mixture was added to ice/water (50 ml.), acidified with 2M hydrochloric acid and extracted with ether (3×20 ml.). The combined extracts were washed successively with water (2×10 ml.), brine (10 ml.), dried (MgSO₄) and evaporated. The residue was purified by chromatography on two 20 cm×20 cm×0.25 mm silica plates (Merck Art. 5715) developing with a mixture of ether/hexane/acetic acid (50:50:0.5 v/v) to give 5(Z)-7-([1,2,4-cis]-4 -methoxy-2-phenylcyclohexyl)heptenoic acid as an oil (58.7 mg.): NMR (CDCl₃): 1.28–2.27 (15H,m), 2.91 (1H, d of t, Jaa=13 Hz, Jae=3 Hz, Jae=3 Hz), 3.28 (1H,m), 3.4 (3H,s), 5.13 (1H,m) 5.27 (1H,m), 7.13–7.33 (5H,m).

EXAMPLE 14

A mixture of 5(Z)-7-cis-2-o-methoxyphenylcyclohexyl)heptenoic acid (0.062 g.) and sodium thiomethoxide (0.140 g.) in N,N-dimethylpropyleneurea (3 ml.) was heated at 140° C. with stirring under argfon for 90 minutes. The reaction mixture was allowed to cool to ambient temperature and then diluted with water (20 ml.). This mixture was extracted with dichloromethane.

The aqueous phase was separated and acidified with acetic acid. Extraction with ethyl acetate followed by drying (MgSO$_4$) and evaporation of the extracts, gave a crude oil, which was purified by flash chromatography using ethylacetate/hexane/actic acid (20:79.5:0.5 v/v) as eluant to give 5(Z)-7-(cis-2-o-hydroxyphenyl-cyclohexyl)heptenoic acid as a colourless oil (0.029 g.); NMR: 1.7 (14H,m), 2.05 (2H,m), 2.25 (2H,m), 3.15 (1H,d), 5.25 (2H,m), 6.75 (1H,dd), 6.9 (1H,m), 7.05 (2H,m)ppm.

EXAMPLE 15-16

Using a similar procedure to that described in Example 13 but replacing the methyl iodide by ethyl bromide and benzyl bromide, respectively, there were obtained:

(Example 15): 5(Z)-7-([1,2,4-cis]-4-ethoxy-2-phenyl-cyclohexyl)heptenoic acid, as an oil in 47% yield; NMR (CDCl$_3$): 1.14-2.38 (18H,m), 2.91 (H, d of t), 3.38 (1H,m), 3.44-3.72 (2H,q), 4.98-5.44 (2H,m), 7.0-7.6 (5H,m); and (Example 16): 5(Z)-7-([1,2,4-cis]-4-benzyloxy-2-phenylcyclohexyl)heptenoic acid, as an oil in 56% yield; NMR (CDCl$_3$): 1.40-2.25 (15H,m), 2.91 (1H,d of t; Jaa=13 Hz, Jae=3 Hz, Jae=3 Hz), 3.49 (1H,m), 4. 5.15 (1H,m), 5.25 (1H,m) and 7.13-7.38 (10H,m).

[Note: Example 15 required the reaction mixture containing ethyl bromide to be heated under reflux for 24 hours].

EXAMPLE 17

A solution of cis-2-(o-methoxyphenyl)cyclohexylacetaldehyde (0.15 g.) in dry tetrahydrofuran (5 ml.) was added under argon with stirring to a solution of the ylid prepared from (4-carboxybutyl)triphenylphosphine (0.86 g) and potassium t-butoxide (0.43 g.) in dry tetrahydrofuran (20 ml.). After the addition the reaction was stirred at ambient temperature for 2 hours. The reaction was quenched by the addition of water (20 ml.) and then acidified by the addition of acetic acid. This mixture was extracted with ether and the extracts dried and evaporated. The resultant gum was purified by flash chromatography using hexane/ethylacetate/acetic acid (90:10:0.5 v/v) as eluant to give 5(Z)-7-(cis-2-o-methoxyphenyl-cyclohexyl)heptenoic acid as a colourless oil (0.11 g.); NMR: 1.6 (14H,m), 2.1 (2H,m), 2.25 (2H,m), 3.25 (1H,m), 3.8, (3H,s), 5.2 (2H,m), 7.0 (4H,m)ppm.

The required starting acetaldehyde derivative was obtained as follows:

A mixture of methyl 2-(o-methoxybenzoyl) propionate (2.22 g.) methyl vinyl ketone (1.6 ml.) and 1,8-diazobicyclo[5:4:0]undec-7-ene (152 μl.) in dry acetonitrile (15 ml.) was stirred under argon for 16 hours. The reaction mixture was evaporated and extracted with ether. The extracts were washed quickly with 0.5M hydrochloric acid, then sodium bicarbonate solution and finally with brine. The extracts were then dried (MgSO$_4$) and evaporated. The residual gum was purified by flash chromatography using ether/hexane (1:1) as solvent to give methyl 6-keto-3-o-methoxybenzoyl-heptanoate (A) (0.54 g.) as an oil; NMR: 1.9 (2H,m), 2.1 (3H,s), 2.4 (3H,m), 2.85 (1H, dd), 3.65 (3H,s), 3.95 (4H,m), 7.3 (4H,m)ppm.

A solution of potassium t-butoxide (0.507 g.) in t-butanol (5 ml.) was added gradually to a stirred solution of (A) (1.2 g.) in t-butanol (10 ml.) maintained under an argon atmosphere and with external cooling to 20°-25° C. The resultant mixture was stirred for 15 minutes and then evaporated to give a sticky solid. This solid was dissolved in water. The resultant solution was acidified (1M HCl) to pH2 and extracted with ether. The extracts were shaken with 10% w/v sodium carbonate solution (3×20 ml.). The combined carbonate extracts were acidified (1M HCl) to give (4-keto- 2-o-methoxyphenyl-cyclohex-2-enyl)acetic acid (B) as a solid precipitate (0.806 g.), m.p. 183°-184° C. NMR: 2.2 (7H,m), 3.5 (1H,m), 3.8 (3H,s), 6.05 (1H,d), 7.05 (4H,m) ppm.

A mixture of B (1.13 g.) and concentrated sulphuric acid (0.1 ml.) in absolute alcohol (12 ml.) was heated under reflux for 2 hours. The reaction mixture was cooled, neutralised by addition of saturated sodium bicarbonate solution and evaporated to dryness. The residue was extracted with ether. The extracts were washed with saturated sodium bicarbonate solution, then with distilled water, dried (MgSO$_4$) and evaporated. The residual gum was purified by flash chromatography using ethyl acetate/hexane (1:4 v/v) as eluant, to give ethyl (4-keto-2-o-methoxyphenyl-cyclohex-2-enyl)acetate (C) as a colourless oil (1.03 g.);NMR: 1.15 (3H,t), 2.25 (6H, m), 3.6 (1H,m), 3.85 (3H,s), 4.05 (2H,q), 6.05 (1H,d), 7.1 (4H,m)ppm.

A mixture of C (1.03 g.), ethylene glycol (0.23 g.) and p-toluenesulphonic acid (0.068 g.) in benzene (60 ml) was heated under reflux for 7 hours using a syphonic extraction apparatus containing dried 3A molecular sieves (4 g.). The solution was then evaporated. The residual gum was dissolved in ether. The solution was washed with saturated sodium bicarbonate solution, then with brine, and was dried (MgSO$_4$) and evaporated. The residual gum was purified by flash chromatography using ether/hexane (1:1 v/v) as eluant to give the ethylene ketal (D) of C as a colourless oil (0.576 g.); NMR: 1.2 (3H,t), 1.9 (2H,t), 2.4 (4H,m), 2.85 (2H,dd), 3.75 (3H,s), 4.0 (4H,s), 4.1 (2H,q), 7.05 (4H,m)ppm.

A solution of D (0.204 g.) in absolute ethanol (20 ml.) was hydrogenated at atmospheric pressure using a 30% w/w palladium on carbon catalyst (50 mg.). After 36 ml. of hydrogen had been consumed (3.5 hours) the catalyst was separated by filtration and washed with absolute ethanol. The filtrate was evaporated and the residue purified by flash chromatography, using hexane/ether (85:15 v/v) as eluant to give ethyl (cis-2-o-methoxyphenyl-cyclohexyl) acetate (E) (0.042 g.); NMR: 1.1 (3H,t), 1.62 (9H,m), 2.2 (1H,dd), 2.65 (1H,m), 3.25 (1H,m), 3.8 (3H,s), 3.9 (2H,q), 6.95 (4H,m)ppm. [The ethylene ketal of ethyl (cis-4-keto-2-o-methoxyphenyl-cyclohexyl)acetate (0.05 g.) was also obtained as a by-product].

A solution of E (0.084 g.) in dry toluene (10 ml.) was stirred at −60° C. and 0.3 ml. of a 1M solution of diisobutylaluminium hydride was gradually added. The reaction mixture was stirred for 30 minutes at −60° C. and then quenched by adding absolute ethanol (0.5 ml.). The mixture was allowed to attain ambient temperature and then was added to an excess of water and ether. The ether layer was dried (MgSO$_4$) and evaporated. The residual oil was purified by flash chromatography using hexane/ether (9:1 v/v) as eluant to give (cis-2-o-methoxyphenyl-cyclohexyl)acetaldehyde as a viscous oil (0.028 g.) which was used without full characterisation.

EXAMPLE 17

An illustration of a pharmaceutical composition suitable for administration to man for therapeutic purposes is a capsule containing a compound of formula I (such as that described in Example 8) or a salt as appropriate (2-300 mg.) together with powdered lactose (596.5-298.5 mg.) and magnesium stearate (1.5 mg.) i.e. 600 mg. of dry ingredients.
Chemical Formulae
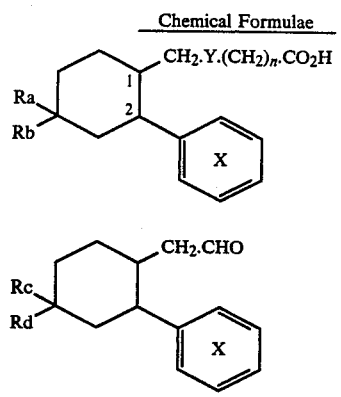
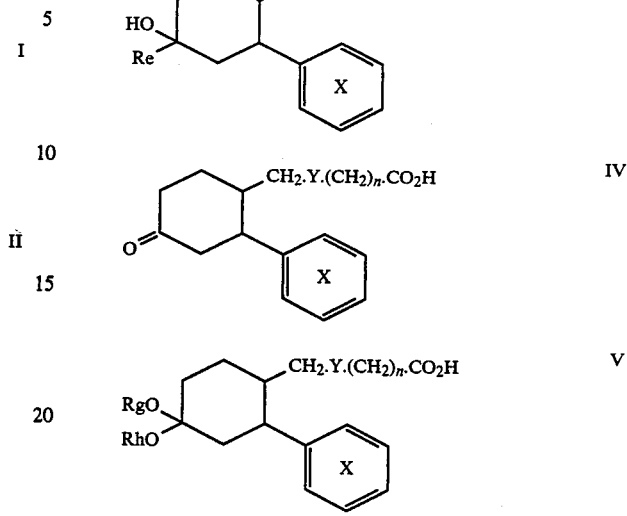
Scheme 1
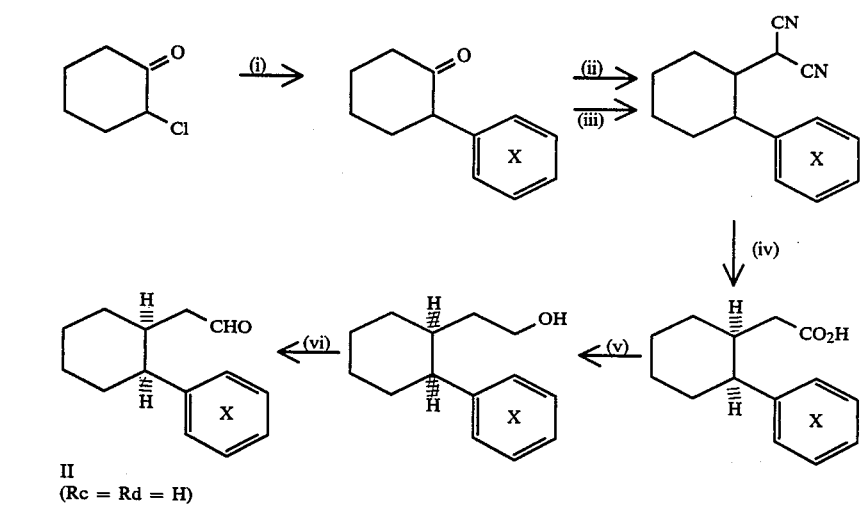
II
(Rc = Rd = H)
Reagents:
(i) 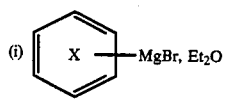 MgBr, Et₂O
(ii) $CH_2(CN)_2$, $NH_4O.CO.CH_3$, $CH_3CO_2H$, toluene at reflux
(iii) $PtO_2$, $H_2$, MeOH
(iv) conc. HCl, $CH_3CO_2H$
(v) $Na.AlH_2(OCH_2CH_2OCH_3)_2$, toluene
(vi) pyridinium chlorochromate, $CH_2Cl_2$

Scheme 2

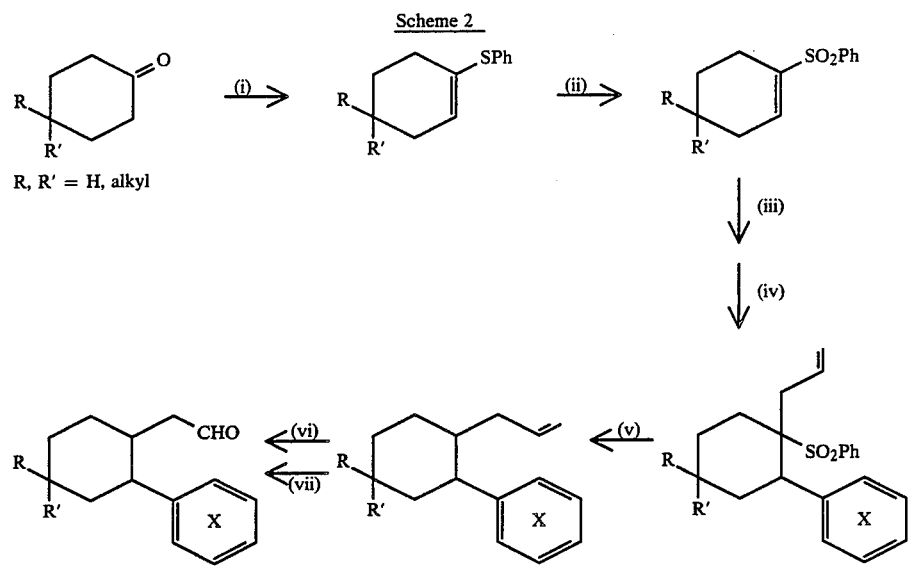

Reagents:
(i) PhSH, p-TsOH, toluene
(ii) 2KHSO$_5$·KHSO$_4$·K$_2$SO$_4$ (iii)

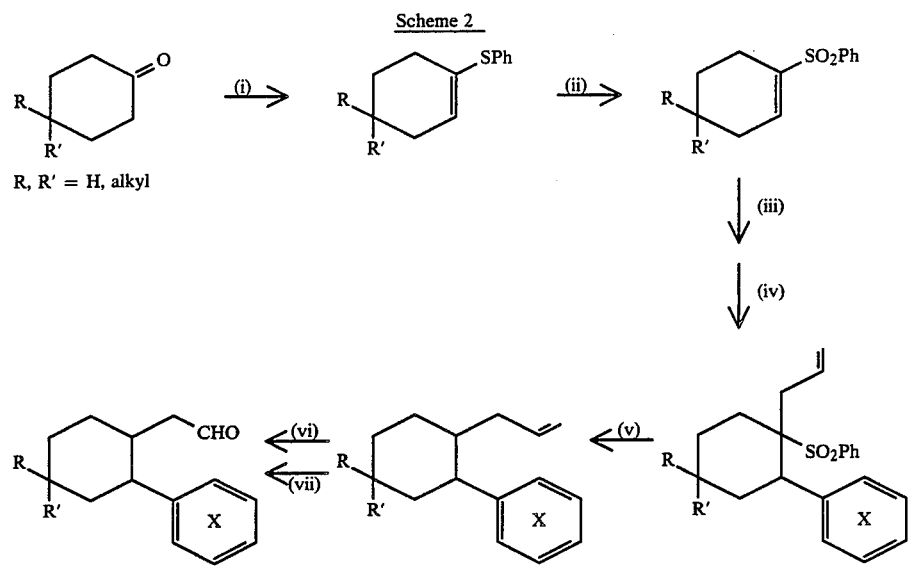

(iv) allylbromide, Et$_2$O
(v) Na$_2$HPO$_4$, THF, MeOH, 6% w/w Na/Hg
(vi) O$_3$, CH$_2$Cl$_2$
(vii) Ph$_3$P, CH$_2$Cl$_2$

Scheme 3

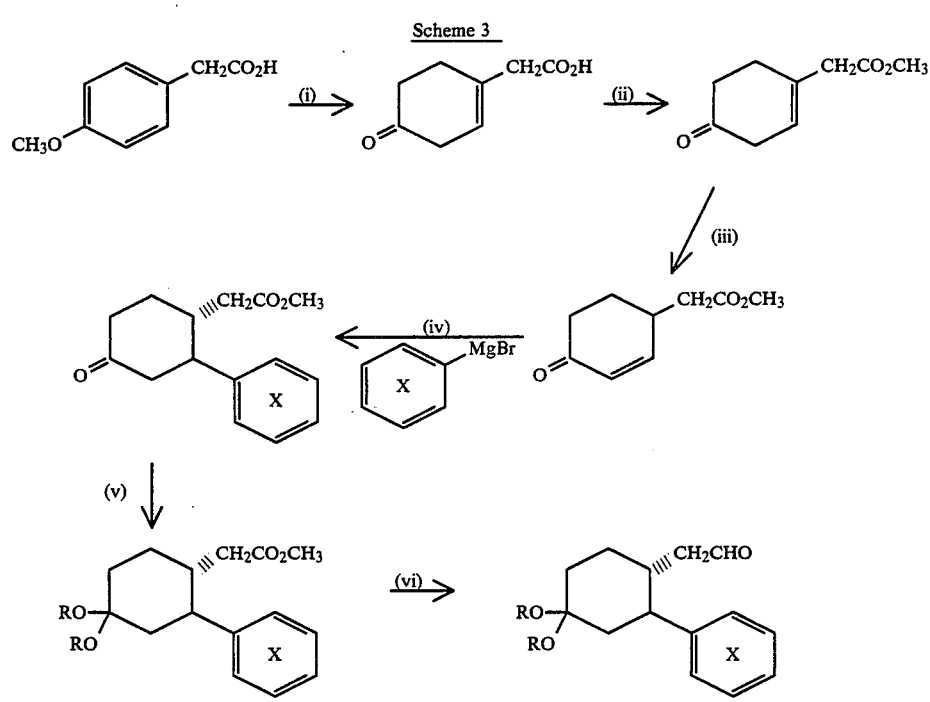

Reagents:
(i) Li, liquid NH$_3$, EtOH, Et$_2$O
(ii) CH$_2$N$_2$, Et$_2$O
(iii) DBU, CH$_3$CN
(iv) Cu$_2$I$_2$, tetrahydrofuran
(v) ROH, p-toluenesulphonic acid, benzene, ΔH
(vi) (i-Bu)$_2$AlH, toluene, −70° C.

Note:
RO = (1–6C)alkoxy
(RO)$_2$ = (2–4C)alkylenedioxy 4,736,057

Scheme 4

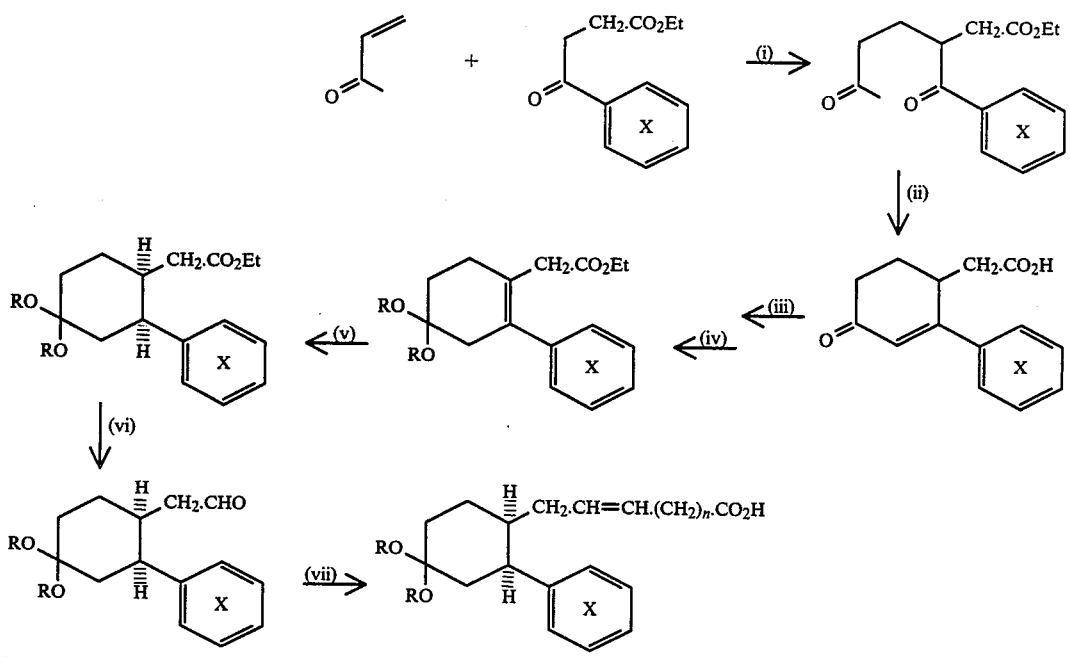

Reagents:
(i) 1,8-Diazabicyclo[5.4.0]undec-7-ene (DBU), MeCN
(ii) $K^{\oplus}$ t-BuO$^{\ominus}$, t-BuOH
(iii) $H^{\oplus}$, EtOH
(iv) *ROH, $H^+$
(v) 5% w/w Pd/C, $H_2$
(vi) (i-Bu)$_2$AlH, toluene, $-70°$ C.
(vii) Ph$_3$P=CH.A.CO$_2$.Na, DMSO
Note:
*RO = alkoxy or (RO)$_2$ = alkylenedioxy Scheme 5

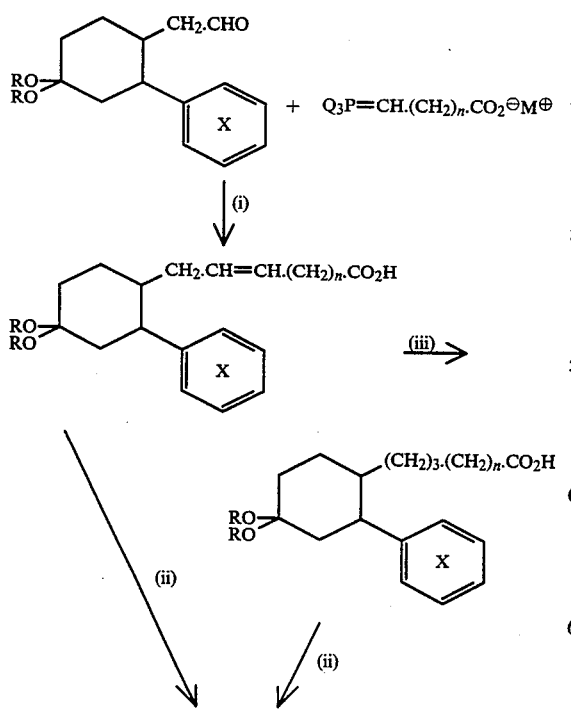

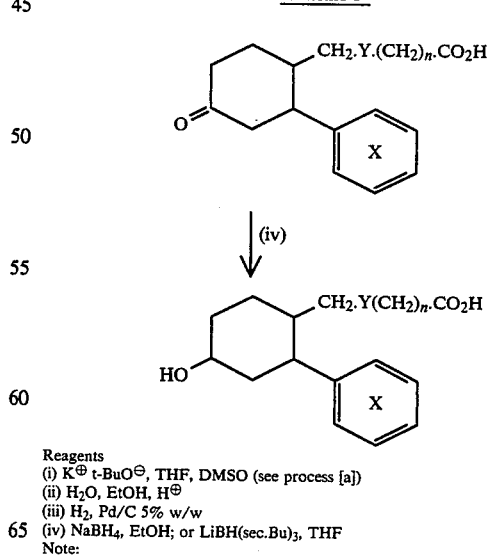

Reagents
(i) $K^{\oplus}$ t-BuO$^{\ominus}$, THF, DMSO (see process [a])
(ii) $H_2O$, EtOH, $H^{\oplus}$
(iii) $H_2$, Pd/C 5% w/w
(iv) NaBH$_4$, EtOH; or LiBH(sec.Bu)$_3$, THF
Note:
RO = alkoxy or (RO)$_2$ = alkylenedioxy
Q = alkyl or aryl e.g. methyl or phenyl

Scheme 6

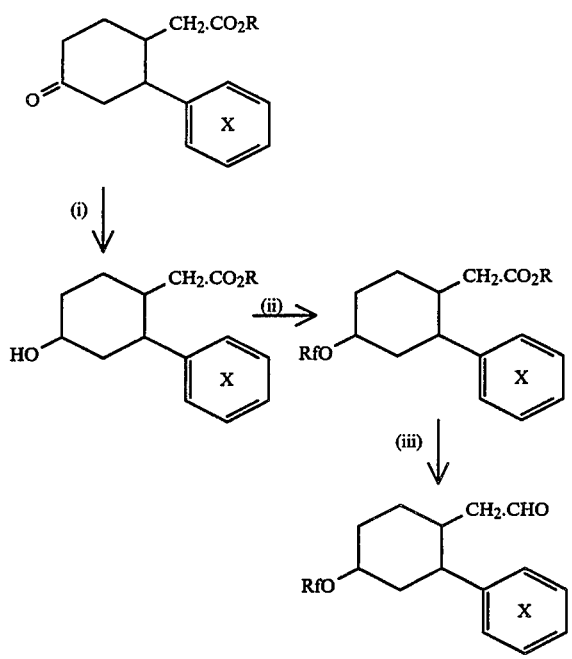

Reagents:
(i) i-PrOH, Al(OPr^i)_3 (R = Me, Et)
(ii) Rf.Z, base e.g. MeI, NaH (see process [b])
(iii) (i-Bu)_2AlH, toluene, −70° C.

What is claimed is:

1. An acid of the formula

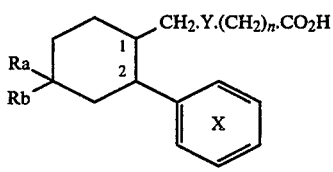

wherein one of Ra and Rb is hydrogen, hydroxy, (1-6C)alkyl, (1-6C)alkoxy, (3-6C)alkenyloxy or phenyl(1-4C)alkoxy and the other of Ra and Rb is hydrogen, (1-6C)alkyl, (1-6C)alkoxy or (3-6C)alkenyloxy; or Ra and Rb together form a (2-4C)alkylenedioxy or oxo group; benzene ring X optionally bears a substituent selected from halogeno, (1-6C)alkyl, (1-6C)alkoxy, hydroxy, (2-6C)alkanoyloxy, (1-6C)alkanoylamino, trifluoromethyl and nitro; n is 3-5; Y is ethylene or vinylene; and in the cyclohexane ring, the substituents at positions 1 and 2 have cis- or trans- relative stereochemistry; or a pharmaceutically acceptable salt, (1-6C)alkyl ester or (1-6C)alkanesulphonamide of said acid.

2. A compound as claimed in claim 1 wherein one of Ra and Rb is selected from hydrogen, hydroxy, methyl, ethyl, propyl, butyl, methoxy, ethoxy, propoxy, butoxy, allyloxy, 2-methylallyloxy, benzyloxy, 1-phenylethoxy and 2-phenylethoxy, and the other of Ra and Rb is selected from hydrogen, methyl, ethyl, propyl, butyl, methoxy, ethoxy, propoxy, butoxy, allyloxy and 2-methylallyloxy; or Ra and Rb together form an ethylenedioxy, trimethylenedioxy or oxo group; and benzene ring X optionally bears a substituent selected from fluoro, chloro, bromo, methyl, ethyl, propyl, isopropyl, butyl, pentyl, hexyl, methoxy, ethoxy, propoxy, butoxy, acetoxy, propionyloxy, butyryloxy, hydroxy, formamido, acetamido, propionamido, trifluoromethyl and nitro.

3. A compound as claimed in claim 1 wherein n is 3 and Y is cis-vinylene.

4. A compound as claimed in claim 1 wherein the substituents at positions 1 and 2 of the cyclohexane ring have cis-relative stereochemistry.

5. 5(Z)-7-([1,2,4-Cis]-4-hydroxy-2-phenylcyclohexyl)heptenoic acid, or a pharamceutically acceptable salt thereof.

6. A pharmaceutically acceptable salt of an acid of formula I claimed in claim 1 selected from alkali metal, alkaline earth metal, aluminium and ammonium salts, and from salts with organic amines and quaternary bases, which form physiologically acceptable cations.

7. A (1-6C)alkyl ester of an acid of formula I claimed in claim 1 which is selected from methyl, ethyl, propyl and butyl esters.

8. A (1-6C)alkanesulphonamide of an acid of formula I claimed in claim 1 which is selected from the methanesulphonamide and ethanesulphonamide.

9. A pharmaceutical composition which comprises an acid of formula I, or a pharmaceutically acceptable salt, (1-6C)alky ester or (1-6C) alkanesulphonamide thereof, as claimed in claim 1; together with a pharmaceutically acceptable diluent or carrier.

10. A method of antagonising one or more of the actions of thromboxane $A_2$ in a warm-blooded animal requiring such treatment which comprises administering to said animal a thromboxane $A_2$ antagonistically effective amount of an acid of the formula I, or a pharmaceutically acceptable salt, (1-6C)alkyl ester or (1-6C)alkanesulphonamide thereof, as claimed in claim 1.

* * * * *